United States Patent [19]

Heslinga et al.

[11] 4,338,417

[45] Jul. 6, 1982

[54] METHOD OF PREPARING A POLYMER MIXTURE, FORMED PRODUCTS OBTAINED THEREFROM AND POLYMER ALLOY

[75] Inventors: Adolf Heslinga, Hd Pijnacker; Pieter J. Greidanus, Mk Leiden, both of Netherlands

[73] Assignee: Nederlandse Centrale Organisatie voor Toegepast-Natuurwetenschappelijk Onderzoek, The Hague, Netherlands

[21] Appl. No.: 159,649

[22] Filed: Jun. 16, 1980

Related U.S. Application Data

[63] Continuation-in-part of Ser. No. 105,750, Dec. 20, 1979.

[30] Foreign Application Priority Data

Dec. 22, 1978 [NL] Netherlands ............................ 7812529
Dec. 5, 1979 [NL] Netherlands ............................ 7908799

[51] Int. Cl.$^3$ ..................... C08L 33/02; C08L 1/12; A61K 47/00; C08F 6/10
[52] U.S. Cl. ..................... 525/197; 424/78; 521/134; 525/192; 525/198; 525/207; 525/194; 528/501
[58] Field of Search ................. 525/197, 198, 207, 192

[56] References Cited

U.S. PATENT DOCUMENTS

| | | | |
|---|---|---|---|
| Re. 27,140 | 6/1971 | Kay et al. ............................ | 525/207 |
| 2,798,053 | 7/1957 | Brown ................................. | 521/38 |
| 3,257,478 | 6/1966 | Jubilee et al. ...................... | 525/207 |
| 3,299,184 | 1/1967 | Whitworth et al. ................. | 525/207 |
| 3,326,864 | 6/1967 | Moore et al. ....................... | 525/207 |
| 3,488,311 | 1/1970 | Burdick et al. ..................... | 525/207 |
| 3,497,574 | 2/1970 | Press .................................. | 525/207 |
| 3,658,752 | 4/1972 | Das et al. ........................... | 525/197 |
| 3,873,643 | 3/1975 | Wu et al. ............................ | 525/197 |
| 3,939,123 | 2/1976 | Matthews ........................... | 528/60 |
| 3,957,908 | 5/1976 | Heslinga et al. ................... | 525/207 |
| 3,983,095 | 9/1976 | Bashaw et al. ..................... | 526/15 |
| 4,160,754 | 7/1979 | Schäpel ............................... | 260/29.4 R |
| 4,192,727 | 3/1980 | Ward .................................. | 204/159.12 |

FOREIGN PATENT DOCUMENTS

| | | |
|---|---|---|
| 7401887 | 8/1974 | Netherlands . |
| 7507186 | 6/1975 | Netherlands . |
| 7710816 | 10/1977 | Netherlands . |
| 7803089 | 3/1978 | Netherlands . |
| 1200106 | 7/1970 | United Kingdom . |

Primary Examiner—H. S. Cockeram
Attorney, Agent, or Firm—Bert J. Lewen

[57] ABSTRACT

Method for preparing a polymer alloy which is stable and homogeneous at high temperatures which comprises a component (a) one or more polymers of high molecular weight, having anhydride groups and component (b) one or more polymers of high molecular weight, having groups which have the ability to interact with hydrogen atoms to form hydrogen bonds. Initially, a solution of component (a) is prepared in an organic solvent and thereafter a solution of component (b) is added. Component (a), in the dissolved state, may be protolyzed in whole or in part, prior to or after the addition of component (b) by the action of protolyzing agents. After the solvent is removed formed products, such as granules, fibres, foils, foam, may be made from the polymer alloy.

20 Claims, 4 Drawing Figures

REACTION EQUATIONS

REACTION EQUATIONS

FIG. 4

METHOD OF PREPARING A POLYMER MIXTURE, FORMED PRODUCTS OBTAINED THEREFROM AND POLYMER ALLOY

RELATED APPLICATIONS

This application is a continuation-in-part of copending U.S. application Ser. No. 105,750 filed Dec. 20, 1979.

The invention relates to a method for preparing a polymer mixture; formed products obtained therefrom, such as granules, fibres, foils, foam; and a polymer alloy.

It has already been proposed to prepare moisture-absorbent and extensively swellable polymers of unsaturated carboxyl compounds, such as maleic anhydride, by polymerizing the carboxyl monomer with a crosslinking agent, such as a polyethylenically unsaturated compound, according to the method specified in U.S. Pat. No. 2,798,053. Such polymers are used as synthetic gums in the preparation of sticky or gel-like aqueous mixtures.

It is also known from British Pat. No. 1,200,106 that certain weakly crosslinked polymers with a large numer of hydrophilic units can be advantageously used as absorbing and binding liquids. As described in U.S. Pat. No. 4,192,727, such polymers, which are slightly crosslinked, partly hydrolyzed polyacrylamides, have been recommended as components of the filling material for disposable diapers and beds and of other similar sanitary products because of their ability to retain appreciably more aqueous liquid under pressure than an equal amount of fluffy cellulose or similar material. In some application of such extensively water-swellable polymers, however, difficulties have been encountered in containing the polymer after it has been saturated with the aqueous liquid.

It is desirable to have an extensively water-swellable, water-insoluble polymer in fibrous form, such as has been described in more detail in U.S. Pat. No. 3,983,095. Further, it is in general desirable to have polymers with an adjustable capacity of moisture absorption.

Furthermore, U.S. Pat. Nos. 4,160,754 and 3,939,123 have described water-swellable and water-absorbent materials obtained by other cross-linking reactions, such as between polyisocyanates and polyols. Moreover, many moisture-sensitive or swellable plastics have been developed on the basis of water-soluble polymers, such as polyacrylic acid, polyacrylamide and derivatives thereof, alone or combined with naturally occurring hydrophilic polymers, such as starch, cellulose and derivatives. These materials are known as synthetic hydrogels. In many cases they are manufactured in the form of powders, fibres, granulates, foils, etc. They are used for, among other things, medical and sanitary purposes. In this context, cf. *Encyclopedia of Polymer Science and Technology*, 15, 273-291.

These as well as the many other water-soluble or water-degradable packaging materials which are now available have major drawbacks. Specifically, processibility at high temperatures (such as 120° to 200° C.), which are customarily used in the processing of thermoplastics, is often very poor. This is particularly so when polymers having side groups are activated at elevated temperatures. Crosslinking reactions often cause the initially thermoplastic characteristics to be lost, so that continuous processing at high temperatures becomes very difficult or impossible to implement.

On the other hand, many hydrophilic polymers, such as polyvinyl alcohol, cellulose, starch and derivatives thereof, have very high melting or softening ranges, or do not melt or soften at all. In such cases, too, the conventional thermoplastic processing techniques cannot be used or are very difficult to operate. In addition, crosslinking reactions or dehydration may take place, causing the original properties of the structures to be irreversibly changed.

Accordingly, there is a need for synthetic polymers having hydrophilic properties comparable to starch, proteins and cellulose which can be prepared and processed according to the available technology for thermoplastics (e.g., extrusion, injection molding, foil extrusion and calendering) without causing untimely irreversible changes or reactions in the polymers.

The invention aims at providing a method of preparing hydrophilic synthetic polymers which eliminates the drawbacks of the prior art preparation methods.

To this end, the method according to the invention is characterized in that a polymer alloy is prepared which is stable and homogeneous up to high temperatures, initially made mainly from component (a) which is one or more polymers of high molecular weight having anhydride groups and component (b) which is one or more polymers of high molecular weight with groups which have the ability to interact with hydrogen atoms to form hydrogen bonds. The term "polymer alloy" is well known in the art. Note particularly the article entitled "Polymer Alloys," *Polymer Science and Technology*, Plenum Press, New York, Vol. 10 (1977).

To prepare the polymer alloy, a solution of component (a) is first prepared in an organic solvent, to which solution component (b) is added. Component (a) in the dissolved state is protolyzed in whole or in part prior to or after the addition of component (b) under the action of protolyzing agents. Thereafter, the solvent is removed. Components (a) and (b) each have molecular weights of at least $10^4$.

In general, component (a) has highly polar characteristics, but is nevertheless insoluble in water. Under the influence of water, however, at certain pH and temperature conditions, it may be converted into a water-soluble polymer by the formation of free carboxyl groups or carboxylate ions. The solubility in water is a function of pH.

A major aspect of the invention is the discovery that a homogeneous polymer alloy can be prepared. Generally speaking, substances of high molecular weight which are made up of different chemical structures are not or only slightly homogeneously miscible in all proportions (cf. among others, *Encyclopedia of Polymer Science and Technology*, 20, 694-697). The preparation of homogeneous polymer alloys was generally considered impossible or very difficult.

Surprisingly, it has now been discovered that a polymer alloy may be prepared from a component (a) which is a high molecular weight polymer of an alkene-unsaturated monomer and a component (b) which is a polymer having an ester side chain.

Component (a) may be at least one high molecular weight polymeric material having an appendant anhydride group and a molecular weight of at least 10,000. Most preferably, this component is made by reacting an alkene-unsaturated monomer with maleic anhydride. The alkene-unsaturated monomer may be of the styrene type having the formula:

wherein R is hydrogen, an alkyl group having from 1 to 6 carbon atoms, or a halo atom; the benzene ring may be substituted with low molecular weight alkyl, hydroxy, nitro or halo groups. The most preferred compound of this class is styrene, though alpha-methyl styrene, para-alpha-methyl styrene, and para-t-butyl styrene may also be used. In addition to styrene-type monomers, another alkene-unsaturated monomer which is preferred in preparing component (a) is methyl vinyl ether. This monomer, when reacted with maleic anhydride, forms a copolymer sold under the trademark Gantrez AN-169, a trademark of GAF Corporation. The component (a) which is a copolymer of styrene and maleic anhydride is referred to hereinafter as (SMA).

Component (b) must be at least one polymeric material having a molecular weight of at least 10,000, which is reactive with hydrogen ions. Examples of such compounds include polymers based on acrylic esters, nitriles and amides, e.g., acrylonitrile, methylmethacrylate, cyclohexylmethacrylate; vinyl and vinylidene halides, e.g., vinyl chloride, vinylidene chloride; vinyl carboxylates, e.g., vinyl acetate, vinyl trimethylacetate, vinyl formate. Furthermore, as polymeric materials, polyesters and nylon may be used. The most preferred are vinyl, cellulose, acrylic and methacrylic esters. Specific examples are: poly(vinyl acetate) (PVAc), cellulose triacetate (CTA), cellulose aceto-butyrate (CAB), poly(ethyl acrylate) (PEtAcr) or poly(methyl metacrylate) (PMMA).

These components (a) and (b) are miscible in all proportions below certain temperatures because of a slight interaction between the polymer species. At a specific temperature, however, segregation or phase separation will take place. This temperature is called the critical temperature, Tc. Tc is a function of the molecular weights of the components and the mutual weight ratio.

Furthermore, it has been found that miscibility at high temperatures (100°–200° C.) can be adjusted by increasing the physical interaction (association) of the polymer components. This increased interaction is brought about by partial hydrolysis (generally protolysis) of component (a), before or after the addition of component (b). The protolysis introduces carboxyl groups along component (a), which furnish hydrogen bonds for the association between components (a) and (b).

By a "partial protolysis" is meant that only a portion of the anhydride groups is opened by use of the protolyzing agent. Generally from 5 to 80% of the anhydride groups are protolyzed, preferably from 10 to 15%. The materials used for protolysis may be water, alcohols, and amines. As a practical matter, these latter compounds have from 1 to 10 carbon atoms.

The preferred degree of protolyzing of component (a) and the ratio between component (a) and component (b) is dependent on a variety of factors and generalizations are difficult. However, the degree of interaction between component (a) and component (b) is directly related to Tc. The higher the Tc, the stronger the interaction between component (a) and component (b).

It is of major importance to conduct the protolyzing of component (a) after component (a) has been dissolved in an organic solvent to get a homogeneous reaction.

The manner of evaporation of the solvent or drying is an important part of the present invention. Specifically, it should be carried out so that the aforementioned increased interaction is maintained. An instructive example of polymer alloys according to the invention consists of (a) a copolymer of styrene and maleic anhydride and (b) poly(vinyl acetate). With this alloy the principal effect of the invention, hereinafter referred to as "solvent alloying", is shown.

In order to further illustrate the invention, the following figures are attached.

Figure 1:
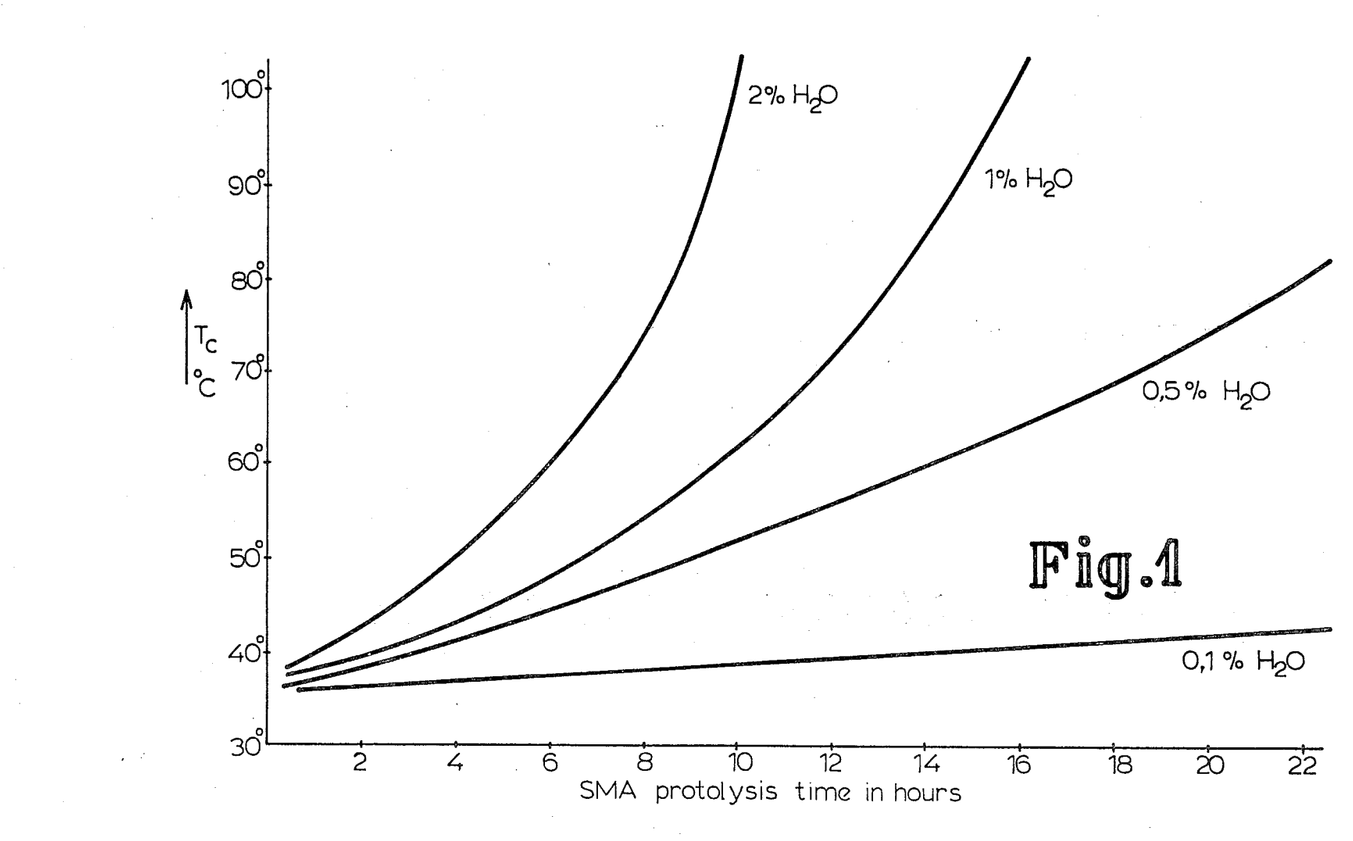
FIG. 1 shows the relationship of protolysis time and critical temperature, Tc, for solutions of polymer alloys containing various amounts of water.

An example of the preparation is as follows:

A mixture of polymers SMA and PVAc is prepared by forming a solution in, for example, butanone. The copolymer (SMA) may be prepared separately by the solution polymerization of styrene and maleic anhydride or a previously prepared polymer may be dissolved. Following the completed polymerization up to the desired molecular weight, partial protolysis of the SMA is effected by adding, for example, water or alcohol to the polymer solution. Heating and catalysts will accelerate the protolysis. Consequently, continued heating of the solution of SMA increases the Tc. The increase of Tc can be expressed as a function of time, concentration and temperature (FIG. 1).

After the protolysis, the PVAc is added to SMA solution, either in solid form or likewise as a solution in butanone, whereupon the polymers are mixed.

Although the concentration of the solution is not critical, a solution of about 20% polymer content is generally used for practical reasons. The dissolving technique is of major importance for obtaining an optimum degree of homogenization. Association of the two components (a) an (b) in the solvent allows the alloying effect to be attained in a short time to a maximum and effective extent. The degree of association of components (a) and (b) is increased by partial hydrolysis (protolysis) of the copolymer as described.

The solid homogeneous polymer alloy may thereafter be obtained by a drying process in which the solvent is evaporated (distilled) in a closed system at temperatures ranging from 100° to 200° C. (generally, from 130° to 160° C.). The distillation or drying process can be accelerated by working under reduced pressure (for example, 10 to 500 mm Hg).

Figure 4:
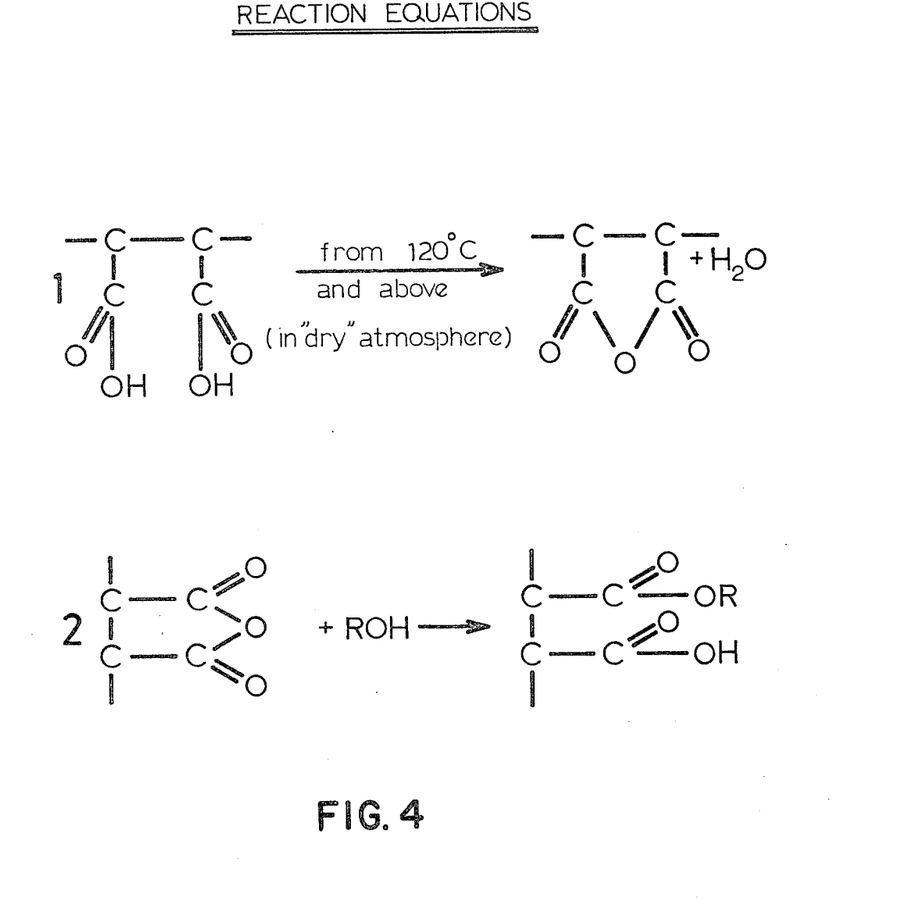
FIG. 4, entitled "Reaction Equations", shows, in Equation 1, the dehydration reaction of the hydrated or hydrolyzed copolymers in a dry atmosphere and Equation 2 shows the formation of a semi-ester during the protolysis reaction.

The drying process is performed in a closed system to facilitate solvent recovery and to insure that the atmosphere has a certain degree of humidity. Preferably, the humidity should be from 0.1 to 0.5% by weight. A fully "dry" environment should be avoided. The reason for this is to avoid the dehydration of the hydrated or hydrolyzed copolymers having anhydride groups into the cyclic anhydride configuration (the reversal of the reaction). (In this connection, cf. reaction equation 1 on FIG. 4.) If dehydration occurs, the association is reduced and phase segregation will take place. The drying process should therefore take place in highly specific conditions. It has surprisingly been found that in certain conditions during drying association is not decreased but, rather, increased. Furthermore, in a closed system the drying process can also be combined with the hydration or hydrolysis reaction.

With the rapid rise of temperature during the drying process, a rapid conversion from anhydride groups to COOH groups occurs in the closed system. As the drying takes place, because the butanone distills off more rapidly, the water content in the solution increases. This, too, accelerates the conversion process.

The relation between the temperature and the state of the resin takes the following course in the drying apparatus:

The Tc rises as a result of fast protolysis by H₂O beyond 100° C.

It is evident that many added substances with reactive functions, such as alcohols, can be chemically bonded to the residual anhydride groups during the drying process. In this connection, cf. the reaction equation 2 on FIG. 4, where a rapid protolysis reaction takes place in the apparatus at an elevated temperature during the drying process to form a semi-ester.

It naturally is also possible to add the widest variety of substances before the drying process: plasticizers, stabilizers, modifiers, adjuvants, fillers, pigments and dyes, lubricants, biologically active substances, etc.

The preferred polymer alloys of the invention at issue have the following properties: thermoplastic; clear; density about 1.2 to 1.3 g/cm$^3$; softening the processing temperatures from 100° to 200° C.; excellent resistance to aliphatic hydrocarbons, oils and fats; soluble in lower alcohols and ketones; and capable of swelling in aromatic hydrocarbons.

The mechanical properties of these polymer alloys are a function of the molecular weights of the components and of the ratio of the two components. For example, a high PVAc content lowers the modulus of elasticity or raises the elongation at break. This is shown in Table A below:

TABLE A

| TENSILE TESTING OF FOIL SAMPLES (POLYMER ALLOY OF SMA AND PVAc) STRIPS (1.5 cm WIDE) LENGTHWISE FROM SAMPLES FIXED LENGTH 10 cm; DRAWING RATE 3cm/min; THICKNESS ca. 0.1 mm | | | | | | | | |
|---|---|---|---|---|---|---|---|---|
| Foil Composition | Yield Stress, kgf/cm$^2$ | | Ultimate Stress, kgf/cm$^2$ | | Elastic Modulus, kgf/cm$^2$ | | Elongation at Break, percent | |
| a/b-SMA/PVAc | Aver. | S.A.* | Aver. | S.A.* | Aver. | S.A.* | Aver. | S.A.* |
| Copolymer No. 10 | | | | | | | | |
| 10/90 | 138 | 9 | 113 | 8 | 7,000 | 2,000 | 250 | 40 |
| 20/80 | 211 | 8 | 139 | 5 | 11,000 | 1,200 | 90 | 40 |
| 30/70 | 425 | 15 | 410 | 80 | 17,000 | 2,500 | 6 | 3.0 |
| 40/60 | — | — | 487 | 4 | 15,000 | 3,000 | 2.3 | 0.2 |
| Copolymer No. 9 | | | | | | | | |
| 10/90 | 97.0 | 3.0 | 101 | 3 | 6,500 | 2,000 | 294 | 8 |
| 20/80 | 185 | 9 | 134.5 | 1.5 | 10,500 | 1,300 | 220 | 25 |
| 30/70 | 343 | 9 | 201 | 10 | 16,500 | 2,000 | 35 | 9 |
| 40/60 | — | — | 470 | 40 | 20,800 | 1,200 | 2.6 | 0.3 |

*S.A. = standard deviation.

The modulus (or the rigidity) can be further lowered by adding plasticizers and/or other modifiers. This is shown in Table B below:

TABLE B

| EFFECT OF PLASTICIZERS: POLYMER RATIO, ca. 1:1 (50/50) PLASTICIZER CONTENT, ca. 30 percent | | | | |
|---|---|---|---|---|
| Plasticizer Code | Ultimate Stress | Yield Stress | Elastic Modulus | Elongation at Break |
| PPA | 135 | 71 | 3000 | 220% |
| SPA | 133 | 152 | 5000 | 59% |
| Polyethylene Comparison Material | 150 | 120 | 2400 | 400% |

PPA = pentaerythritol diacetate-dipropionate
SPA = sorbitol triacetate-tripropionate The new type of polymer alloys of the invention can be processed by using the customary techniques for extrusion from melts and apparatus or techniques for casting from organic solvents. Foils can be fabricated according to known foil blowing techniques. Extrudates and granulates may be obtained by standard extrusion techniques.

Fibres can be manufactured according to the usual techniques; monofilaments, for example, from the melts by dry or wet spinning techniques on the basis of direct coagulation from organic solvents in water or aqueous solutions.

The new compositions of the invention posses the advantage of being extrudable from a melt, either as such or in combination with suitable plasticizers. Suitable plasticizers are here defined as those substances which are adequately compatible with the polymer mixtures and do not give rise to undesired exudation, phase segregation, reactions, etc. Examples are the phthalate type, e.g., dibutyl phthalate and dioctyl phthalate, and the ester type, e.g., glycerine triacetate, glycerol ester and citric acid ester.

The polymer alloys have both hydrophobic and hydrophilic groups. This manifests itself in a typical characteristic, e.g., swellability, particularly in water (see FIG. 3). Swellability of polymer mixtures is evidence of the interaction of the polymer components on a molecular scale (alloying) and also the strong interaction between the different polymer species.

The polymer alloy also has the properties of polyanhydride resins; the presence of residual anhydride group causes the alloy to be reactive even in solid form, so that secondary chemical reactions are possible. Secondary reactions are possible, for instance, with water, alcohols, ammonia, amines and epoxy compounds. (In this connection, cf. the reaction equation 2 of the formula sheet.) These reactions are used in order to improve the processability of the alloys during processing (e.g., extrusion).

A few percents, i.e., 1 to 5 wt. %, of fatty alcohol such as stearyl alcohol may be added to the polymer solution before drying. The formed stearyl esters act during processing as internal, nonexuding lubricants. Clearly, very many modifications, both with regard to chemical and to physical properties, are possible in this manner by means of secondary reactions. The hydrophilic as well as the hydrophobic characteristics can thus be increased and decreased.

The polymer alloys are stable in dry conditions and when stored at normal atmospheric conditions with respect to temperature and relative humidity (50 to 60 percent). However, upon prolonged exposure to air of high humidity or in direct contact with water, a gradual conversion takes place from the anhydride group to the free dicarboxylic acid. The polarity (hydrophilic character) thus increases while the modulus (brittleness), measured in dry conditions, rises simultaneously. As a result of the conversion of the polyanhydride to polyacid or polyelectrolyte, the material assumes the properties of a stable hydrogel. The degree of swelling in water is a function of the degree of ionization of the composition of the polymer alloy, the polymer ratio and of the pH of the aqueous medium. Maximum swelling takes place at, for example, a pH of from 6 to 8, and minimum swelling at a pH of from 2 to 3 (in buffered solution). This phenomenon is reversible and is comparable with the familiar behaviour in water of proteins, such as gelatin and keratin.

The hydrogel accordingly possesses the characteristic properties of a polyelectrolyte and can also function, for example, in hydrogel form, as an ion exchanger by binding multivalent metal ions such as Ca, Cu, Zn and Cd. The hydrogels and xerogels fabricated by hydrolysis from the polymer alloys are stable because of the extensive interaction of component (b) with the hydrolyzed or ionized component (a).

The polyanhydride-polymer alloy can be rapidly converted into a hydrogel polyelectrolyte by reaction with strong organic or inorganic bases such as NaOH and KOH, and especially by ammonia, ammonia-in-water solutions, and organic amines. Crosslinking takes place in reactions with bi- or polyfunctional compounds, such as glycols (preferably, lower aliphatic glycols), di- and polyamines. The degree of swelling of the hydrogels can thus be varied as a result of reactions with both mono- and polyfunctional reactive compounds.

The polymer alloys according to the invention can be used for manufacturing synthetic products having a variety of properties.

The material can be in the form of granules, fibres, foils, powders and other forms known in the processing technology of polymeric materials. Of particular importance is the conversion by water into substances having hydrogel properties (or polyelectrolyte properties).

Especially important is the use of fibrous or powdery material in the form of a polyelectrolyte or salt for moisture absorption. Also possible is the use of hydrogels, formed in secondary reactions, as ion exchangers.

As a result, the polymer alloys are particularly suitable for manufacturing polymer compositions for the controlled release of active constituents, specifically, under the action of water. Both the speed and the degree of swelling affect the delivery rate of the active constituents. The delivery rate naturally is also a function of form and size of the polymer mixtures (granules, powders, foils, fibres, etc.). Active substances may comprise such products as insecticides, fungicides, herbicides, biocides, feromones, repellents for the control of pests, plant diseases or the attack on plants by insects and/or other harmful organisms. Another application is for the controlled delivery of pharmacologically active substances.

If the polymer alloys are prepared in fibrous form, they can be converted by secondary reaction with strong bases into fibres having a high swelling capacity or moisture absorbency in water.

The completed, water-insoluble and water-swellable fibres are suitable for many purposes. These fibres can primarily be used in the manufacture of absorbent layers for sanitary products.

The above application can likewise be implemented by forming the polymer alloys into foils, films of thin sheets or strips. The swellability or absorbency is primarily a function of the ratio of the two polymers in the polymer alloy. Elevated concentrations of component (a) increase the swellability after secondary hydrolysis or ionization to form the hydrogel structures.

Furthermore, the polymer alloy according to the invention may comprise an additional component, such as the active materials noted above, a reactive component for modification of the polymer alloy during its preparation, or a foaming agent for forming a porous structure. As additional material, a filler, such as carbon black, chalk, fibres, can be added after or during the preparation of the polymer alloy.

EXAMPLE I: Preparation of the Copolymer SMA in Butanone by Solution Polymerizations In a vessel having a capacity of about 50 l, 30 l (25 kg) of methylethyl ketone (MEK), 3120 g of styrene, 3000 g of maleic anhydride, and 7.5 g of azo-bis-isobutyronitrile (catalyst) were successively mixed. The vessel was equipped with a heating jacket, a stirrer, a thermometer and a thermal safety device. The contents were heated while being stirred continuously. Initially, the contents were heated to 60° C. over a period of one hour and thereafter held at 60° C. for 2 hours; at 70° C. for 1 hour; and at 80° C. for 3 hours. The total polymerizing time was about 7 hours. The product had a viscosity of about 450 centipoises, a solids content of about 20% by weight, and a critical segregation temperature, Tc, of 41° C. measured with PVAc solution. (See Example II and FIG. 1.)

It will be understood that the degree of polymerization can be varied by altering the catalyst concentration and the reaction temperature.

By measurements of the intrinsic viscosity, the molecular weight was determined to be about 10,000 to 100,000 (*J. of Applied Polymer Science* 20: 1619 [1976]).

The solid polymer can be obtained by evaporation of the solvent or by precipitation in excess methanol.

EXAMPLE II: Partial Hydrolysis of the Copolymer SMA of Example I in Solution to Raise the Critical Segregation Temperature, Tc Upon completion of the polymerization of SMA as described in Example I, to 20% samples of the SMA solution MEK, sufficient water was added, with vigorous stirring, to prepare separate samples having water contents of about 0.1, 0.5, 1 and 2%, respectively. These water-containing solutions were heated for about 20 to 30 hours at 75° C. During heating the critical segregation temperature, Tc, was determined for the mixtures of the samples and poly(vinyl acetate) (PVAc) solution. FIG. 1 shows the rise of Tc for the PVAc/SMA mixture (the extent of protolysis) as a function of the water concentration and the protolysis time at 75° C.

The effect of temperature and water content on the rise of Tc was illustrated by the finding that the Tc of a PVAc/SMA mixture in MEK containing 1% water rose to 100° C. after 40 days of storage at 20° C., while a comparable mixture containing 2% water when heated to 75° C. obtained a Tc value of 100° C. after only 8 hours.

A series of samples were prepared by mixing approximately equal parts of the copolymer solution (20% SMA in MEK) and, respectively, a poly(vinyl acetate) solution, PVAc (M70, Hoechst); a cellulose triacetate solution, CTA (Tenite I, Eastman Kodak); a cellulose aceto-butyrate solution, CAB (Tenite II, Eastman Kodak); and a poly(ethylacrylate), PEtAcr, all of the latter in a 20% MEK solution. To the foregoing solution 1% water was added and the solutions were heated to 75° C. for differing protolysis times.

Figure 2:
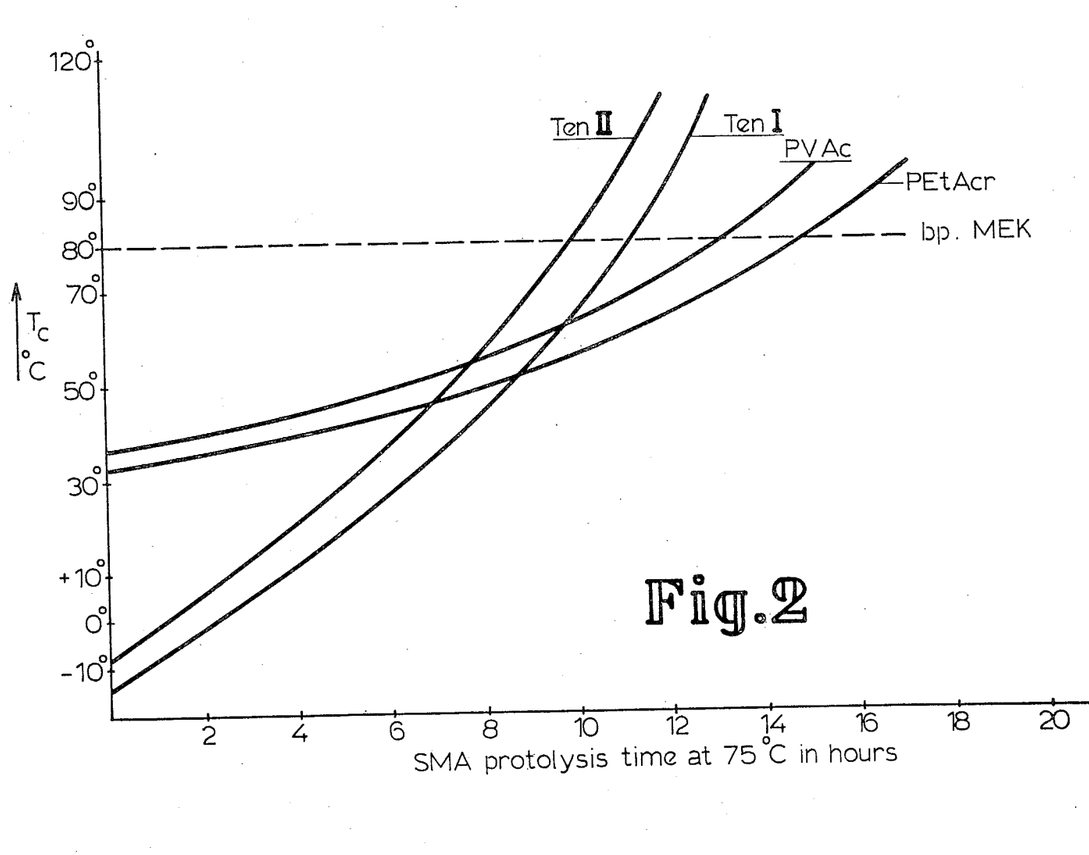
FIG. 2 shows the relationship of protolysis time and critical temperature for solutions of polymer alloys containing copolymers of styrene-maleic anhydride and, respectively, poly(vinyl acetate) cellulose triacetate, cellulose acetobutyrate and poly(ethyl acrylate).

FIG. 2 shows the rise of Tc as a function of protolysis time at 75° C. At Tc the mixtures suddenly turned turbid as a result of segregation.

EXAMPLE III: Preparation of the Polymer Alloy (30:70 Proportion)

10 kg of the 20% copolymer solution of Example I was protolyzed with 10 g water at about 75° to 80° C. for about 16 hours. The Tc rose from 100° to 110° C. This protolyzed copolymer solution, in a vessel (boiler) having a capacity of 50 l, was mixed with 19.6 kg of MEK and 4.66 kg of solid PVAc. The PVAc was Mowilith-70, a suspension or bead polymerizate of Hoechst (Frankfort, Germany). The SMA/PVAc mixing proportion was 30:70. The solid PVAc was dissolved with slow stirring at a temperature of about 15° to 20° C. until a clear solution had been formed. The total solution of the polymer blend was 34.30 kg having a solid matter content of 20%.

Naturally it is possible to carry out the mixing operation with a PVAc solution in MEK. Predissolved PVAc has the advantage of rapid mixing with copolymer solution. Clearly, any desired polymer proportions can be rapidly obtained according to the above procedure.

In the drying process about 1000 kg of the polymer blend were dried with air in an industrial dryer (Luwa Filmtruder). Before drying, about 2 kg of stearyl alcohol (internal, non-exuding lubricant; $C_{18}H_{37}OH$) were stirred into this solution, in order to improve the processability of the solid alloy during processing. Use may naturally be made of other similar dryers as well.

Solid polymer alloy prepared following Example III has a density of from 1.2 to 1.3 $g/cm^3$, and a modulus of elasticity, depending on moisture content and mixture ratio, of from 2,000 to 10,000 $kgf/cm^2$ (viscous to hard).

The granulate can be processed in standard degassing extruders (double-screw), allowing the residual moisture content or solvent to be even further reduced.

Thermal stability tests show a slight increase in viscosity after 1 to 2 hours at 150° C., and some crosslinking after 1 hour at 190° C. The colour remains light yellow. Moisture absorption at high humidity (100 percent relative humidity) is about 5 percent for 30:70 polymer alloy; in boiling water, after 1 hour, about 10 percent. Under normal conditions, the material is stable and permanently thermoplastic.

EXAMPLE IV:

Using the Luwa Filmtruder and the polymer alloy mentioned in Example III, the following drying tests were carried out:

| Test No. | Input, kg/h | Wall temp., °C. | Vacuum mm of Hg | Yield of solid polymer blend kg/h | Appearance of polymer blend |
|---|---|---|---|---|---|
| 1 | 75 | ca. 160 | 300 | 17 | turbid |
| 2 | 60 | ca. 160 | 400 | 14 | slightly turbid |
| 3 | 60 | ca. 180 | 400 | 15 | clear |
| 4 | 50 | ca. 180 | 500 | 12 | clear |
| 5 | 75 | ca. 180 | 200 | 18 | slightly turbid |

The solid matter content of the extrudate formed from the above dried product was about 98 percent. The original Tc was about 100° C.

An additional 1 percent of water was added to about 1000 kg of resin mixture of Example III, followed by 2 hours of stirring and heating at 70° to 80° C. As a result, the critical temperature, Tc, rises to above 140° C.

| Test No. | Input, kg/h | Wall temp., °C. | Vacuum mm of Hg | Yield of solid polymer blend kg/h | Appearance of polymer blend |
|---|---|---|---|---|---|
| 6 [optimum] | 75 | ca. 160 | 300 | 16 | clear |
| 7 | 60 | ca. 190 | 200 | 15 | slightly turbid |

Test no. 6 shows the optimum drying, while in test no. 7 the drying was carried too far and the Tc dropped again.

These examples clearly indicate that the clear homogeneous polymer alloy is only obtained under specific conditions.

EXAMPLE V:

Starting from the solution of polymer alloys of Example III, drying tests have also been carried out with a small laboratory closed roller dryer, set up horizontaly and having two rollers with a screw. The input was about 7 kg/h (20 percent solution); the wall temperature from 140° to 150° C.; and the vacuum, 300 to 400 mm of Hg. The yield of polymer alloy was about 1.5 kg/hr. Its appearance was slightly turbid.

The resultant polymer alloy formed a continuous extrudate having a solid matter content of about 98 to 99 percent. The residual moisture content was 0.5 to 1 percent. The extrudate can be granulated immediately upon cooling.

EXAMPLE VI: Test with Solution of Polymer Alloy having a Tc of 80° C.

The dryer of Example V was charged with a polymer alloy solution prepared from the copolymer solution according to Example I and PVAc (Mowilith-70) in the proportion of 30:70. Drying was carried out in the conditions of test no. 5 in Example IV. The extrudate was now fully white, opaque and of heterogeneous composition. The appearance was the result of phase segregation of the polymer components. In contrast with clear extrudates, the extrudates of Example VI did not swell.

EXAMPLE VII: Test for Demonstrating the Increase of Tc During Drying (Homogeneous and Clear End Product)

Two percent of water was added to the copolymer solution of Example I (percentage of total substance), and the mixture was heated for 8 hours at about 80° C. Tc was now about 90° C. This was followed by mixing with PVAc and MEK so that the proportion of polymers was 50:50.

Drying in the apparatus of Example V was carried out at an input of 5 kg/hr, a temperature of 150° C., and under a vacuum of 400 mm Hg. The yield was 1 kg/hr and the product was colourless to light yellow and clear.

EXAMPLE VIII: Preparation of Polymer Alloy Using Poly(Methyl Vinyl Ether/Maleic Anhydride)

This example shows tests with poly(methyl vinyl ether/maleic anhydride) (Gantrez AN-169) as component (a)

and cellulose aceto butyrate (Tenite II) and polyvinyl acetate (M70) as component (b).

The copolymer is dried for about 5 hours at a temperature of 130°–140° C. in order to obtain the pure anhydride form of the copolymer. The dried copolymer is dissolved in dry MEK to obtain a 20% solution. The resultant solution of component (a) is mixed with a 20% MEK solution of Tenite II. The Tc is about 5°–10° C. The copolymer is then hydrolyzed by the addition of 1–2% water at a temperature of about 20° C. After 1 week the Tc = 50°–60° C.; after 2 weeks it is greater than 100° C.

The same test is carried out with poly(methyl vinyl ether/maleic anhydride) as component (a) and polyvinyl acetate as component (b), both as 20% solution in MEK. The mix ratio of component (a) to component (b) is about 50:50. The initial Tc = 70° C. After 1 week with 2% H$_2$O at 20° C., it increases to 120°–130° C. The increase of Tc ± 50°–60° C. is because of partial hydrolysis. After swelling at a pH of 7 a stable hydrogel is obtained.

EXAMPLE IX: Preparation of Blown Foil (from Polymer Alloy plus Plasticizer)

A solution of polymer alloy was prepared according to the method described and was composed of 50/50 SMA/PVAc polymer (1:1). Tc of the solution of polymer alloy exceeds 120° C. About 10 percent (related to dry matter content) of glycerin triacetate were added prior to desiccation. Following drying according to Example V, granulate was obtained from which blown foil was prepared by extrusion from a ring-shaped slit mold.

Properties of Foil: Thickness of foil, 50 to 60 u; clear; modulus of elasticity, 2,000 to 3,000 kgf/cm$^2$; elongation, 200 to 250 percent; ultimate stress, about 100 kgf/cm$^2$.

The elasticity of the foils of polymer alloys is largely a function of the moisture content of the material and the environment. Sensitivity to moisture can be controlled by the methods described on the basis of the nature of the plasticizers, modifiers, etc.

EXAMPLE X

A polymer alloy was prepared as described in Example IX except the proportion of polymers was 30:70 and the plasticizer was 5% dibutyl phthalate (on polymer basis). The foils had properties similar to that in Example IX.

EXAMPLE XI: Preparation of Fibres (Wet Spinning Method)

A solution of polymer alloy was prepared in MEK having a solid matter content of about 40 percent. The viscosity of the solution was 35,000 to 40,000 cps.

Using prior-art techniques and methods, the solution of polymer alloy was spun as a spinning liquid by wet-state injection into water as a coagulating bath of about 20° C. The spinnerette had 15 apertures with a diameter of 0.05 mm. The solution ejected formed fibres in the form of monofilaments, which could be continuously wound.

The resultant strand had about 5 to 8 dtex (gr/10,000/m) after conditioning at a 65% relative humidity, and the moisture content was 2 to 3 percent at 20° C. (dtex is a measure for filament thickness).

EXAMPLE XII: Melt-spinning Text

From the granulate obtained according to Example VII a fibrous polymer alloy was produced by known melt-spinning techniques in conventional apparatus. The fibres are ionized by post-treatment with ammonia or organic amines (obtaining then electrolytic properties), as a result of which a high water absorbency is obtained, the degree depending on the proportion of the polymers. The swelling capacity (/V) may range from 10 to 100 grammes water/grammes polymer alloy in deionized water.

In the polyelectrolyte form (being in the form of polyions), the fibers have properties of ion exchangers.

EXAMPLE XIII

To 20% of solution of a polymer alloy in MEK according to Example III was added 10% of Chlorfenvinphos (Birlane concentrate Shell insecticide) based on the solid polymer content. The mixture was dried under the conditions described in Example IV, Test No. 3.

The result consisted of 1.6 kg of dry extrudate, which was subsequently granulated. Part of the granules were ground to powder. The granules as well as the powder were used as a control agent for a soil insecticide. The delivery rate of the active substance can be regulated by partial or complete ionization of the polymer alloy, for example by water, ammonia, bases or other protolytic substances. The delivery rate can also be regulated by adjusting the releasing surface area (cf. powder and granules).

As has been shown in Examples V and VI, as well as in Examples II, III, IV and VII, homogeneous blending, i.e., alloying, is possible only if the drying process has been carried out at temperatures below the critical segregation temperature, Tc, of the polymer mixture. The homogeneity of the solid blend can be determined by conversion of the blend into a hydrogel by ionization in water with pH 7.0–7.5. (In homogeneous blends it will not swell.)

EXAMPLE XIV: Preparation of Hydrogel (a) The material of the invention prepared according to Example IV (Test Nos. 3, 4 or 6) can be converted by dilute (1%) ammonia or other bases into a solid hydrogel. This is shown by immersing about 4 grammes of extrudate (platelet, ca. 4×2×0.5 cm) for about 24 hours in an amount of a 1% ammonia solution sufficient to cause swelling. After the preliminary swelling for ca. 24 hr., swelling was continued in neutral water. The water was replenished until maximum swelling had been attained (final pH=7.0 to 7.5).

A stable hydrogel was formed having maximum swelling in neutral water of about 25 to 30 times the original dry weight. The water content of the hydrogel was about 96 to 97 percent. (30:70 polymer alloy.)

Figure 3:
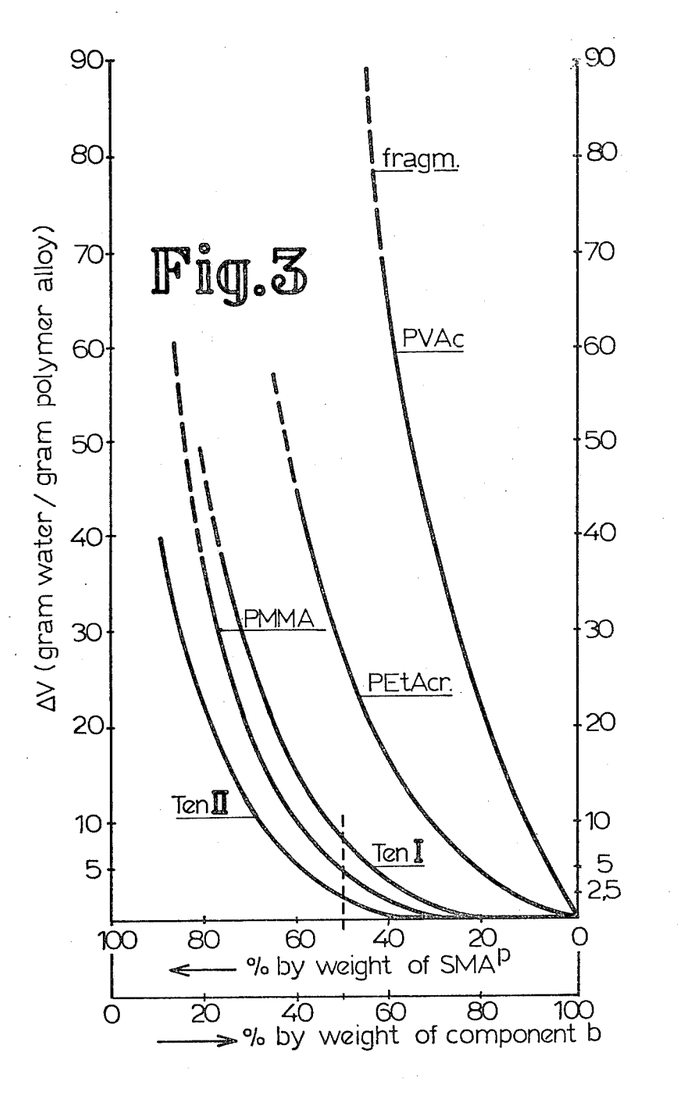
FIG. 3 shows the degree of swelling in water of hydrogels in relation to the ratio of the components (a) and (b).

(b) A second polymer alloy was prepared as follows: Solutions in MEK of PVAc (M70, Hoechst), cellulose triacetate (Tenite I, Eastman Kodak), cellulose acetobutyrate (Tenite II, Eastman Kodak), polyethyl acrylate, PEtAcr (synthesized in the laboratory) and poly(methylmetacrylate), PPMA (Plexiglas, Rohm and Haas and Lucite, Dupont), component (b) (total amount ca. 20 percent), were mixed with SMA, component (a), solutions in MEK according to Example I, being respectively partly protolyzed to Tc values beyond 100° C. In FIG. 3 this protolyzed compound is indicated by SMA$^p$ (p=protolyzed). The solid polymer alloys were prepared by drying the respective polymer mixture solutions at about 70° to 80° C. All solid samples were clear; no segregation occurred. From these solid polymer alloys samples (films about 0.5 mm thick) hydrogels were prepared by the technique described in Example XIII a). The equilibrium take-up of water or degree of swelling (Δ/V) in water of pH ca. 7.0–7.5 was measured as function of component ratio (a:b). The results are given in FIG. 3.

The volume increase (Δ/V) is shown to be a function of the a:b ratio as well as of the whole molecular structure, i.e., physicalchemical properties of component (b). It is also clearly demonstrated that the hydrophility, i.e., moisture absorbing capability of the various polymer alloys, can be adjusted by mixing more or less component (a) in the polymer alloy.

We claim:

1. A polymer alloy comprising a first component which is at least one high molecular weight polymer having appendant anhydride groups, at least a portion of which have been protolyzed to form hydrogen atoms thereon, and a second component which is at least one high molecular weight polymer derived from a monomeric ester having vinyl unsaturation, and having reactive groups thereon, at least a portion of which are interacted with the aforementioned hydrogen atoms, so that the two components are linked by hydrogen bonds.

2. The polymer alloy of claim 1 wherein the first component is at least one copolymer of an alkeneunsaturated monomer and maleic anhydride.

3. The polymer alloy of claim 2 wherein the first component is a copolymer of styrene-maleic anhydride or of methyl vinyl ethermaleic anhydride.

4. The polymer alloy of claim 1, 2 or 3 wherein the second component is a polymer of a vinyl carboxylate, an acrylate ester, or a methacrylate ester.

5. The polymer alloy of claims 1, 2, 3 or 4 wherein the ratio of the first component to the second component is from 1:100 to 100:1.

6. The polymer alloy of claim 1 wherein a biologically active substance is added to the polymer alloy during preparation.

7. The polymer alloy of claim 1 wherein the polymer alloy is modified by reacting with a base or a crosslinking agent.

8. The polymer alloy of claim 1 wherein the polymer alloy contains a filler.

9. A material useful for making hydrogels which is the reaction product of the polymer alloy of claim 1 and an organic or inorganic amine.

10. The material of claim 9 wherein the amine is ammonia.

11. A process for preparing a polymer alloy which comprises reacting a first component which is at least one high molecular weight polymer having a molecular weight of at least 10,000 and having appendent anhydride groups at least a portion of which are protolyzed to form hydrogen atoms thereon with a second component which is a high molecular weight polymer derived from a monomeric ester having vinyl unsaturation, and having a molecular weight of at least 10,000 and having reactive sites thereon which are reactive with said hydrogen atoms, said reaction taking place in an organic solvent; and thereafter, removing said solvent from said reaction product in a closed system and thereby obtaining the polymer alloy.

12. The process of claim 11 wherein the anhydride groups are protolyzed with water.

13. The process of claim 11 wherein the solvent is removed in an atmosphere having a humidity of from 0.1 to 0.5 wt. % and at a temperature of from 100° to 200° C.

14. The process of claim 11 wherein the solvent is removed at a temperature of from 130° to 160° C. and at a pressure of from 10 to 500 mm Hg.

15. The process of claim 11 wherein the first component is at least one copolymer of an alkene-unsaturated monomer and maleic anhydride and the second component is a polymer of an unsaturated ester.

16. The process of claim 15 wherein the first component is a copolymer of styrene-maleic anhydride or of methyl vinyl ether-maleic anhydride.

17. The process of claim 15 wherein the second component is a polymer of a vinyl carboxylate, an acrylate ester, or a methacrylate ester.

18. The process of claim 11 wherein a biologically active substance is added to the polymer alloy during preparation.

19. The process of claim 11 wherein the polymer alloy is modified by reacting with a base or a crosslinking agent.

20. The process of claim 11 comprising the additional step of adding a filler.

* * * * *